US010717707B2

United States Patent
Syvret et al.

(10) Patent No.: US 10,717,707 B2
(45) Date of Patent: Jul. 21, 2020

(54) SYNTHESIS OF 2,2,2-TRIFLUOROETHANETHIOL

(71) Applicant: Arkema Inc., King of Prussia, PA (US)

(72) Inventors: Robert George Syvret, Allentown, PA (US); Craig Alan Polsz, Newtown, PA (US); Dana Lee Swan, Norristown, PA (US); Vijay R. Srinivas, Exton, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/238,548

(22) Filed: Jan. 3, 2019

(65) Prior Publication Data

US 2019/0135740 A1    May 9, 2019

Related U.S. Application Data

(63) Continuation of application No. 15/500,654, filed as application No. PCT/US2015/043060 on Jul. 31, 2015, now abandoned.

(60) Provisional application No. 62/034,214, filed on Aug. 7, 2014.

(51) Int. Cl.
*C07C 319/02* (2006.01)

(52) U.S. Cl.
CPC ................. *C07C 319/02* (2013.01)

(58) Field of Classification Search
CPC .................................................. C07C 319/02
See application file for complete search history.

(56) References Cited

U.S. PATENT DOCUMENTS

| | | | |
|---|---|---|---|
| 2,894,991 A | 7/1959 | Barr et al. | |
| 3,006,964 A * | 10/1961 | Oesterling | C07C 309/06 568/24 |
| 3,088,849 A | 5/1963 | Friedlander | |
| 6,680,398 B1 | 1/2004 | Boswell et al. | |
| 6,765,109 B1 | 7/2004 | Brown et al. | |

FOREIGN PATENT DOCUMENTS

CN    1425649    6/2003

OTHER PUBLICATIONS

Halpern et al. ("Top 10 Opportunities to Improve Process Performance and Profit Using Phase Transfer Catalysis", Industrial Phase Transfer Catalysis, Issue 16, 2002, pp. 1-14).*
Sizov, A. Yu., et al; Russian Chemical Bulletin, International Edition, vol. 55, No. 7, pp. 1200-1208, Jul. 2006. "Synthesis and Reactivity of Fluorine-Containing Thiols and Thioacyl Halides".
Harris, John F. and Sheppard, William A.; Journal of Organic Chemistry, (1961) vol. 26 (2) pp. 354-358; "The Reductive Thiolation of Fluorinated Carbonyl Compounds".
Fukui, Kenichi et al; 10-Organic Chemistry, 1958 (pp. 3661-3662) "Reaction of Alkyl Halides with Sodium Hydrosulfide in Ethylene Glycol"—Abstract Only
F. Drahowzal et al, "Some Knowledge of Sulfonic Acid Esters" From the institute of Organic Chemical Technology, Veinna Technical University, Oct. 1951.
135 Helmut Zinner: Note on the Preparation of Mercaptans from the Institute of Organic Chemistry and Biochemistry of Universit of Jeana, Apr. 1953.
136 Richard Kuhn, Aseline Gauhe and Hans Helmut Baer: an N-containing Testrasaccharide from Human Milk, from Max-Planck Institute for Medical Research, Heidelberg Institute of Chemistry, Apr. 1953.
Zhang, Zhen; Synthesis and Fundamental Research of Isopropyl Mercaptan with Sodium Hydrosulfide; Chinese Master's Theses Full Text Database, Engineering Science and Technology I; Issue 3, pp. 3, 19-21; Mar. 15, 2012.

\* cited by examiner

*Primary Examiner* — Rosalynd A Keys
(74) *Attorney, Agent, or Firm* — Steven D. Boyd

(57) ABSTRACT

A method of making $CF_3CH_2SH$, comprising a step of reacting $CF_3CH_2X$, wherein X is halide or tosylate, with MSH, where M is an alkali metal such as Na or K, to yield $CF_3CH_2SH$.

21 Claims, No Drawings

SYNTHESIS OF 2,2,2-TRIFLUOROETHANETHIOL

The present application is a continuation application of U.S. patent application Ser. No. 15/500,654 filed Jan. 31, 2017 which is the national phase under 35 USC 0 371 of prior PCT International Application Number PCT/US2015/043060 filed Jul. 31, 2015 which designated the United States of America and claimed priority to U.S. Provisional Patent Application Ser. No. 62/034,214 filed Aug. 7, 2014.

FIELD OF THE INVENTION

The invention relates to methods for synthesizing 2,2,2-trifluoroethanethiol ($CF_3CH_2SH$), which is a useful etchant for electronics applications.

DISCUSSION OF THE RELATED ART

The fluorothiol compound 2,2,2-trifluoroethanethiol, which has the chemical structure $CF_3CH_2SH$, has utility as an etchant in the manufacture of various electronic products and as an intermediate in the synthesis of various organic compounds. It is also useful in creating self-assembled monolayers on electrode surfaces and the like. However, to date a commercially viable process for synthesizing 2,2,2-trifluoroethanethiol using readily available starting materials has not been described or developed.

BRIEF SUMMARY OF THE INVENTION

One aspect of the present invention provides a method of making $CF_3CH_2SH$, comprising a step of reacting $CF_3CH_2X$, wherein X is a leaving group selected from the group consisting of halide and tosylate, with MSH, wherein M is an alkali metal. For example, X may be Cl and/or M may be Na.

The reaction may be carried out in at least one organic solvent, in particular in at least one polar organic solvent such as dimethyl sulfoxide, dimethylacetamide, N-methylpyrrolidone, dimethylformamide and/or ethylene glycol. The reaction may be carried out in the presence of at least one phase transfer catalyst, in particular a tetra alkyl ammonium salts such as tetra-n-butylammonium bromide, methyltrioctylammonium chloride (Aliquat®) and mixtures thereof.

The reactant MSH may be reacted in molar excess with the $CF_3CH_2X$. For example, at least two moles of MSH per mole of $CF_3CH_2X$ may be reacted. In one embodiment, the reaction may be conducted at a temperature within a range of about 70° C. to about 110° C. The $CF_3CH_2X$ and MSH may be reacted for a period of time of from about 1 hour to about 5 hours, for example.

The reaction may be carried out at a pressure above atmospheric pressure, for example in a pressurized vessel. Hydrogen sulfide ($H_2S$) may be additionally present during the reacting of the $CF_3CH_2X$ and MSH.

Reacting $CF_3CH_2X$ and MSH may yield a reaction product mixture comprised of $CF_3CH_2SH$ and at least one by-product selected from the group consisting of $(CF_3CH_2)_2S_2$ and $(CF_3CH_2)_2S$. In this embodiment of the invention, the method may additionally comprise a further step of separating $CF_3CH_2X$ from the reaction product mixture and/or additionally comprise a further step of separating the at least one by-product from the reaction product mixture. The at least one by-product separated from the reaction product mixture may be reacted with a hydrogenating agent to form $CF_3CH_2SH$.

One particular embodiment of the invention provides a method of making $CF_3CH_2SH$, comprising a step of reacting $CF_3CH_2Cl$ with a molar excess of NaSH in a reaction medium comprised of one or more polar organic solvents at a temperature of from about 70° C. to about 110° C. for a time of from about 1 to about 5 hours. One particular embodiment of the invention provides a method of making $CF_3CH_2SH$, comprising a step of reacting $CF_3CH_2Cl$ with a molar excess of NaSH in a in the presence of a phase transfer catalyst at a temperature of from about 70° C. to about 110° C. for a time of from about 1 to about 5 hours.

DETAILED DESCRIPTION OF CERTAIN EMBODIMENTS OF THE INVENTION

A compound or mixture of compounds corresponding to the chemical formula $CF_3CH_2X$, wherein X is a halide or tosylate, is utilized as one of the starting materials in the process of the present invention. Preferably, X is Br (bromine) or Cl (chlorine). Such compounds are well known in the art and may be synthesized using conventional methods or obtained from commercial sources. For example, the compound $CF_3CH_2Cl$ is sold under the designation HCFC-133a.

The MSH starting material functions as a source of the nucleophile $HS^-$, which reacts with $CF_3CH_2X$ to displace the halide or tosylate X thereby substituting a thiol functional group (—SH) for the halide or tosylate. MSH is suitably an alkali metal hydrosulfide, wherein M is an alkali metal. Preferably, M is K (potassium) or, even more preferably, Na (sodium). Any suitable source of the MSH may be utilized as the starting material. For example, sodium hydrogen sulfide hydrate, which is readily available from multiple commercial sources at low cost, may be used. If so desired, the MSH may be generated in situ in the initial reaction mixture. Generally speaking, it will be advantageous to react at least one mole of MSH per mole of $CF_3CH_2X$. Under at least certain reaction conditions, using a significant molar excess of MSH relative to $CF_3CH_2X$ may help to improve the yield of the desired product 2,2,2-trifluoroethanethiol. For example, at least 2, at least 3, at least 4 or at least 5 moles of MSH per mole of $CF_3CH_2X$ may be used.

The reaction of the $CF_3CH_2X$ and MSH starting materials may be carried out in the presence of one or more solvents, in particular one or more organic solvents. The solvent(s) may function as a reaction medium in which one or both of the stalling materials is dissolved. The amount of solvent relative to the starting materials is not believed to be critical and may be optimized in accordance with standard experimental procedures. In one embodiment, the solvent is a polar organic solvent or combination of polar organic solvents. The solvent may be non-protic, but in other embodiments of the invention a protic solvent may be utilized. Examples of suitable solvents include, but are not limited to, sulfoxides such as dimethylsulfoxide, amides such as dimethylacetamide, N-methylpyrrolidone and dimethylformamide, and glycols such as ethylene glycol and combinations thereof. Following completion of the reaction between the $CF_3CH_2X$ and the MSH, the solvent(s) may be recovered from the reaction product mixture by distillation or other suitable methods and recycled for use in the reaction to make the desired 2,2,2-trifluoroethanethiol. The recovered solvent may be subjected to any known or conventional purification method prior to such re-use.

The reaction of the $CF_3CH_2X$ and MSH starting materials may be carried out in the presence of one or more transfer catalysts, in particular tetra alkyl ammonium salts such as tetra-n-butylammonium bromide and methyltrioctylammonium chloride (Aliquat®) and mixtures thereof.

In one embodiment of the invention, hydrogen sulfide ($H_2S$) is additionally present during reaction of the MSH and $CF_3CH_2X$. The presence of hydrogen sulfide has been found to help favor the production of 2,2,2-trifluoroethanethiol, relative to bis-sulfide by-product. Formation of the desired product $CF_3CH_2SH$ occurs according to Equation (1) below:

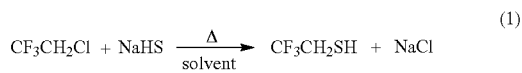
(1)

Formation of the by-product bis-sulfide, $(CF_3CH_2)_2S$, occurs when the target product $CF_3CH_2SH$ further reacts with NaSH according to Equations (a) and (b) below:

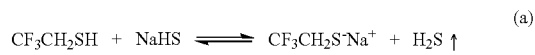
(a)

(b)

Thus, having $H_2S$ present helps to prevent the formation of by-products by shifting to the left the equilibrium depicted in (a). In one embodiment of the invention, sufficient $H_2S$ is present in the sealed reactor such that the partial pressure of $H_2S$ above the liquid reaction medium is greater than the saturation partial pressure. Thus, in a sealed reactor system, a "head pressure" of $H_2S$ is preferably maintained that ensures that the reaction liquid is, at the very least, completely saturated with $H_2S$ and such that the maximum concentration of $H_2S$ possible is in solution. In that way, the greatest (positive) influence on equilibrium (a) will be realized.

The MSH and $CF_3CH_2X$ reactants, together with solvent(s) and optionally $H_2S$ or phase transfer catalyst and optionally $H_2S$, are combined and heated for a time and at a temperature effective to achieve reaction between the MSH and $CF_3CH_2X$, thereby forming the desired product $CF_3CH_2SH$. In one embodiment, the MSH is initially combined with the solvent(s) or phase transfer catalyst(s) to form a reaction mixture, with the $CF_3CH_2X$ then being introduced into the reaction mixture by any suitable method (e.g., bubbling the $CF_3CH_2X$ into the reaction mixture sub-surface as a gas). In another embodiment, a solvent or phase transfer catalyst is introduced into a vessel or other apparatus and cooled to below room temperature, with the $CF_3CH_2X$ and then the MSH then being sequentially introduced before heating the reaction mixture up to the temperature effective to initiate reaction between the MSH and the $CF_3CH_2X$. Typically, reaction temperatures above room temperature are used in order to achieve a satisfactory rate of reaction. For example, the reaction mixture may be heated at a temperature of from about 70° C. to about 110° C., although lower or higher temperatures may also be used depending upon the selection of reactants, solvent, phase transfer catalyst, pressure and other reaction parameters. Reaction (heating) times of from about 1 to 5 hours are typically sufficient to obtain a useful yield of $CF_3CH_2SH$, but the selection of other reaction parameters may influence the optimum reaction time. Where reaction temperatures above room temperature are employed, it will generally be advantageous to carry out the reaction in a vessel or other apparatus capable of being pressurized, in view of the relative volatility of the $CF_3CH_2X$ reactant (when X is a halide) and the optional $H_2S$ component. In such embodiments of the invention, the maximum pressure within the vessel or other apparatus may range from about 1 to about 400 psig. The method of the present invention may be carried out in a batch, semi-continuous or continuous manner. In one embodiment of the process, a first portion of MSH is reacted with $CF_3CH_2X$ in a first stage, followed by the addition of a second portion of MSH and further reaction in a second stage (i.e., the MSH may be combined with the $CF_3CH_2X$ portion-wise or step-wise). The reaction mixture may be stirred or otherwise agitated while contacting the MSH and $CF_3CH_2X$.

The reaction product mixture obtained as a result of the above-described reaction between the MSH and the $CF_3CH_2X$ may be subjected to any desired purification, neutralization, separation, fractionation and/or recovery step(s) to isolate in purified form the $CF_3CH_2SH$ product. The other components of the reaction product mixture may be recycled, disposed of, or further reacted as may be desired. For example, the solvent(s) may be separated and reused, as may any unreacted $CF_3CH_2X$. Under at least certain reaction conditions, sulfide-containing by-products such as $(CF_3CH_2)_2S_2$ and/or $(CF_3CH_2)_2S$ may be generated in combination with the desired $CF_3CH_2SH$. Although such by-products may be desirable for certain end-uses, in one embodiment of the invention they are treated with a suitable hydrogenating agent to convert them into additional quantities of $CF_3CH_2SH$. Hydrogenating agents and conditions suitable for converting such sulfide by-products to the corresponding thiol compounds are well known in the art. For example, the Zn/HCl hydrogenation conditions described in U.S. Pat. No. 2,894,991 (incorporated herein by reference in its entirety for all purposes) may be utilized. Catalytic hydrogenation methods such as those described in U.S. Pat. No. 5,728,887, for example (each of which is incorporated herein, by reference in its entirety for all purposes), may also be employed.

The present invention comprises:
1. A method of making $CF_3CH_2SH$, comprising a step of reacting $CF_3CH_2X$, wherein X is a leaving group selected from the group consisting of halide and tosylate, with MSH, wherein M is an alkali metal.
2. The method of claim 1, wherein X is Cl.
3. The method of any one of the preceding claims, wherein M is Na.
4. The method of any one of the preceding claims, wherein the reacting is carried out in at least one organic solvent.
5. The method of any one of the preceding claims, wherein the reacting is carried out in at least one polar organic solvent.
6. The method any one of the preceding claims, wherein the reacting is carried out in at least one solvent selected from the group consisting of dimethylsulfoxide, dimethylacetamide, N-methylpyrrolidone, dimethylformamide, ethylene glycol and combinations thereof.
7. The method of claim 1, wherein the reacting is carried out in the presence of a phase transfer catalyst.

8. The method of any one of claims 1 and 7, wherein the phase transfer catalyst is a tetraalkyl ammonium salt.

9. The method of any one of claims 1, 7 and 8, wherein the tetraalkyl ammonium salt is selected from the group consisting of tetra alkyl ammonium sails such as tetra-n-butylammonium bromide, methyltrioctylammonium chloride and mixtures thereof.

10. The method any one of the preceding claims, wherein MSH is reacted in molar excess with $CF_3CH_2X$.

11. The method any one of the preceding claims, wherein at least two moles of MSH per mole of $CF_3CH_2X$ are reacted.

12. The method of any one of the preceding claims, wherein the reacting is conducted at a temperature within a range of about 70° C. to about 110° C.

13. The method of any one of the preceding claims, wherein $CF_3CH_2X$ and MSH are reacted for a period of time of from about 1 hour to about 5 hours.

14. The method of any one of the preceding claims, wherein the reacting is carried out at a pressure above atmospheric pressure.

15. The method of any one of the preceding claims, wherein $H_2S$ is additionally present during the reacting of $CF_3CH_2X$ and MSH.

16. The method of any one of the preceding claims, wherein the reacting is carried out in a sealed reactor with the $CF_3CH_2X$ and the MSH present in a liquid reaction medium and wherein sufficient $H_2S$ is present in the sealed reactor such that the partial pressure of $H_2S$ above the liquid reaction medium is greater than the saturation partial pressure.

17. The method of any one of the preceding claims, wherein reacting $CF_3CH_2X$ and MSH yields a reaction product mixture comprised of $CF_3CH_2SH$ and at least one by-product selected from the group consisting of $(CF_3CH_2)_2S_2$ and $(CF_3CH_2)_2S$.

18. The method of any one of the preceding claims, additionally comprising a further step of separating $CF_3CH_2X$ from the reaction product mixture.

19. The method of any one of the preceding claims, additionally comprising a further step of separating the at least one by-product from the reaction product mixture.

20. The method of any one of the preceding claims, additionally comprising a further step of reacting the at least one by-product separated from the reaction product mixture with a hydrogenating agent to form $CF_3CH_2SH$.

21. A method of making $CF_3CH_2SH$, comprising a step of reacting $CF_3CH_2Cl$ with a molar excess of NaSH in a reaction medium comprised of one or more polar organic solvents at a temperature of from about 70° C. to about 110° C. for a time of from about 1 to about 5 hours.

22. The method of claim 21, wherein $H_2S$ is additionally present during the reacting of $CF_3CH_2Cl$ and NaSH.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein

EXAMPLES

Example 1

This example demonstrates the reaction of 2,2,2-trifluoro-1-chloroethane (HCFC-133a) with NaSH to obtain 2,2,2-trifluoroethanethiol, according to equation 1 below:

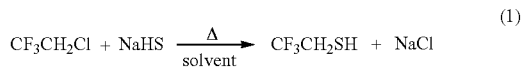

A number of experiments were run in NMP (N-methylpyrrolidone) solvent with varying amounts of NaSH. These experiments were run in a 150 ml Chemglass glass pressure reactor containing a magnetic stir bar and equipped with a pressure gauge and a pressure relief valve. The reactions were heated and stirred using an oil bath on top of an IKA digital hot plate/stirrer. The $CF_3CH_2Cl$ was bubbled into the reaction mixture sub-surface as a gas. Reactions were typically done on a 3-5 gram (HCFC-133a) scale and conversion was determined by measurement of the $^1H$ NMR signal of HCFC-133a (SM in Table 1) and comparing to the $^1H$ NMR signal of the solvent. The product distribution was determined by comparison of the unique $^{19}F$ NMR signals for the desired thiol product, $CF_3CH_2SH$ (I) and the by-products bis-sulfide $(CF_3CH_2)_2S$ (II) and bis-disulfide $(CF_3CH_2)_2S_2$ (III). The results from these experiments are summarized in Table 1 below.

TABLE 1

Summary of Results of Reactions of HCFC-133a with NaSH in NMP (N-methylpyrrolidone) Solvent

| Expt. | NaHS Equiv. | Max. Temp. | Max. psig | Time (hours) | $^1H$ NMR % Conv. | Product Distribution (Mol %) from $^{19}F$ NMR | | | |
|---|---|---|---|---|---|---|---|---|---|
| | | | | | | SM | I | II | III |
| 1b | 2* | 80 | 26 | 3 | 98 | 7 | 52 | 41 | <1 |
| 1c | 3 | 90 | 9 | 2 | 100 | 0 | 61 | 39 | <1 |
| 1d | 4 | 90 | 15 | 2 | 100 | 0 | 68 | 32 | <1 |
| 1e | 5 | 90 | 11 | 3 | 100 | 0 | 73 | 27 | <1 |

*1 equivalent of Acetic Acid was added in Experiment 1b.

This example shows that the amount of desired thiol relative to other products can be increased by increasing the ratio of NaSH relative to HCFC-133a.

Example 2

Using similar methodology as described in Example 1, the nucleophilic displacement of the tosylate (OTs=p-toluenesulfonate) group from $CF_3CH_2OTs$ using the nucleophile $SH^-$ (supplied from NaSH) was investigated as a route to prepare the target compound (I), $CF_3CH_2SH$, according to equation 2 below:

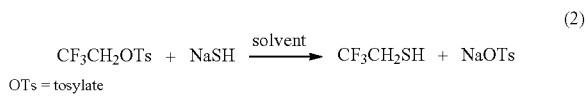

OTs = tosylate

Experiments were run in NMP solvent and the results are summarized in Table 2 below.

TABLE 2

Summary of Results of Reactions of $CF_3CH_2OTs$
with NaSH in NMP (N-methylpyrrolidone) Solvent

| Expt. | NaHS Equiv. | Max. Temp. | Max. psig | Time (hours) | $^1$H NMR % Conv. | Product Distribution (Mol %) from $^{19}$F NMR | | | |
|---|---|---|---|---|---|---|---|---|---|
| | | | | | | SM | I | II | III |
| 2a | 1 | 80 | 4 | 3 | 95 | 19 | 25 | 56 | <1 |
| 2b | 4 | 90 | 0 | 3 | 100 | 0 | 53 | 47 | <1 |

Example 3

Using similar methodology as described in Example 1, the nucleophilic displacement of the chlorine atom from HCFC-133a, $CF_3CH_2Cl$, using the nucleophile $SH^-$ (supplied from NaSH) was investigated in a variety of polar solvents. All reactions were run in a 150 ml Chemglass reactor with magnetic stirring and heated at 90° C. for three hours. HCFC-133a was introduced sub-surface to the solvent. A one mol excess of $NaSH$—$H_2O$ was used for all experiments. The results are summarized in Table 3 below. Product distribution is expressed in mol % and was determined by 19F NMR spectroscopy.

TABLE 3

Summary of Results of Reactions of HCFC-
133a with NaSH in different solvents

| | | Product Distribution (Mol %) from $^{19}$F NMR | | |
|---|---|---|---|---|
| Expt. | Solvent | Thiol | bis-sulfide | bis-disulfide |
| 3a | DMSO | 19 | 58 | 23 |
| 3b | DMSO* | 28 | 44 | 27 |
| 3c | Dimethylacetamide | 50 | 44 | 6 |
| 3d | NMP | 44 | 51 | 5 |
| 3e | DMF | 47 | 47 | 6 |

Example 4

This example demonstrates the reaction of HCFC-133a added as a gas with NaSH in solvent with added $H_2S$ over-pressure.

A 300 ml Hastelloy "C" stirred pressure reactor (Parr Instrument Company) was used for the reaction of HCFC-133a with NaSH in solvent and using an over-pressure of $H_2S$. The added $H_2S$ is intended to reduce the formation of bis-sulfide and bis-disulfide by-products.

Sodium hydrogen sulfide hydrate, $NaSH.H_2O$, 9.38 g (126.6 mmol), was dissolved in N-methylpyrrolidone (NMP) solvent (135.25 g) and trifluorotoluene (TFT), 2.45 g (16.8 mmol) was added to the mixture as an internal standard. The reactor was sealed and HCFC-133a, 16.24 g (137 mmol) was added as a gas over ten minutes. During the addition, the temperature increased from 18 to 23° C. Hydrogen sulfide, $H_2S$, 7.47 g (219.2 mmol) was then added over seven minutes during which the temperature remained at 23° C. while the pressure increased to 10 psig. The reactor was heated to 90° C. and held at that temperature for six hours during which time the pressure increased to 65 psig. After the specified time, the heat was shut off and the reactor contents were stirred overnight as the reactor cooled to ambient temperature. The next day, the reactor was vented and sampled for $^{19}$F NMR analysis. The $^{19}$F NMR results showed 42% (I) product yield and 23% (II) by-product. There was also 11% unreacted HCFC133a.

An additional 2.33 g (31.5 mmol) of $NaSH.H_2O$ was dissolved in 11.89 g of NMP and added to the reactor. The reactor was sealed and $H_2S$, 9.06 g (265.9 mmol), was added. The reactor was heated, reaching a maximum temperature of 138° C. and a pressure of 350 psig. The reactor was heated an additional five hours at 130° C. and then permitted to cool overnight. The next day the reactor was vented and sampled for $^{19}$F NMR analysis. The $^{19}$F NMR results showed 45% (I) product yield and 23% (II) by-product. There was no unreacted HCFC133a indicating a complete conversion.

Example 5

This example illustrates the reaction of HCFC-133a added as a liquid with NaSH in solvent with added $H_2S$ over-pressure.

Similar methodology as that described in Example 4 was used for this Example. Thus, sodium hydrogen sulfide hydrate, $NaSH.H_2O$, 11.28 g (152.3 mmol) was dissolved in N-methylpyrrolidone (NMP) solvent (136.3 g) and trifluorotoluene (TFT), 2.54 g (17.4 mmol) was added to the mixture as an internal standard. The reactor was sealed and $H_2S$, 13.36 g (392.0 mmol) was then added over 7 minutes during which time the pressure increased to 25 psig. The reactor was then heated to 90° C. while the pressure increased to 120 psig. Following this, HCFC-133a, 15.0 g (126.6 mmol) was added over the course of 15 minutes as a liquid by way of a high pressure liquid delivery pump. Following the addition of HCFC-133a, the pressure was 120 psig @ 90° C. The reaction mixture was stirred at 90° C. for an additional 2 hours and then permitted to cool with stirring overnight. The following day the reactor was vented and sampled to permit $^{19}$F NMR analysis of the reaction mixture. F-19 NMR results showed 31% product (I) yield and 5% by-product (II) yield.

Example 6

This example illustrates the reaction of HCFC-133a added as a liquid with NaSH in solvent with added $H_2S$ over-pressure.

A 75 ml Parr Reactor (Hastelloy C) equipped with a pressure gauge, thermocouple and pressure relief valve was used for this example. Ethylene glycol (45.08 g) was charged to the reactor. The bottom portion of the reactor was cooled in dry ice and 5.60 g (47.3 mmol) of HCFC-133a was bubbled into the cooled solvent. Sodium hydrogen sulfide hydrate 11.28 g (152.3 mmol) was added to the reactor together with trifluorotoluene 1.0802 g (7.4 mmol). A magnetic stir bar was placed inside the reactor and it was sealed. The reaction mixture was stirred and heated to 165° C. for three hours during which time the pressure reached its maximum at 290 psig after two hours. Following the specified time, heating was shut off and the contents of the reactor stirred overnight as they cooled to ambient temperature. The following day the reactor was vented and sampled for $^{19}$F NMR analysis. The reaction yield was determined using trifluorotoluene as an internal standard. The yield of desired product (I) was 18 mol % while the yield of by-products (II) and (III) were 4.9 and 3.4 mol %, respectively.

Example 7

This example illustrates the reaction of CF$_3$CH$_2$OTs with NaSH in a Phase Transfer Catalyzed (PTC) System.

Example 7A

Reaction Done in a 150 mL Glass Reactor

A 150 ml Chemglass pressure reactor was charged with 8.53 g CF$_3$CH$_2$OTs (33.6 mmol), 46.29 g toluene (0.503 mmol), and 0.8525 g trifluorotoluene (5.8 mmol). Trifluorotoluene is used as internal standard for $^{19}$F NMR analysis. The reactor was then charged with: 0.97 g tetra-n-butylammonium bromide, (n-Bu)$_4$NBr (3.0 mmol); and 1.19 g Aliquat®® 336, methyltrioctylammonium chloride (2.9 mol) phase transfer catalysts. Sodium hydrogen sulfide hydrate, NaHS.H$_2$O (5.72 g/77.2 mmol) was charged to a 50 ml beaker with a magnetic stir bar and dissolved with water (12.70 g/705.6 mmol). After dissolving, concentrated HCl (5.79 g @ 36%=2.08 g/57.2 mmol) was added slowly to the stirred mixture. The pH decreases from 10 to 7.8 during addition. The NaSH/H$_2$O solution was subsequently charged to the 150 ml glass reactor. A magnetic stir bar was inserted and the reactor sealed. The reactor head was equipped with a pressure gauge and pressure relief valve. The glass reactor was placed in an oil bath at a temperature of 90° C. The mixture is heated in the bath at 90° C. for four hours resulting in a final pressure of 36 psig at the end of the heating time period. The next day the reaction mixture was analyzed by $^{19}$F NMR spectroscopy. The conversion (disappearance of SM) was 49.4% and the product (I) yield was 44.5%. The reaction mixture was re-heated to 90° C. for four hours and the resulting final pressure at the end of heating was 39 psig. After cooling overnight the reaction mixture was sampled for analysis by $^{19}$F NMR. The conversion was 56.6% and the product (I) yield was 50.6 mol %. Additional NaHS.H$_2$O (1.42 g/19.2 mol) was added and the reaction mixture was re-heated to 90° C. for an additional hour. The resulting pressure was 33 psig at the end of the heating period. After cooling overnight, the pressure in the reactor was still 8 psig so the reaction mixture was cooled with dry ice to −10° C. which resulted in the pressure being reduced to 0 psig. Analysis of a sample by $^{19}$F NMR indicated the conversion was 77.4% and the product (I) yield was 67.5 mol %. Additional NaHS.H$_2$O (0.5 g/6.8 mmol) was added and the reaction mixture was reheated to 90° C. for an additional four hours with a final pressure of 35 psig at the end of heating time period. After cooling overnight, the pressure in the reactor was still 5 psig so the reactor was vented to the scrubber and sampled for analysis by $^{19}$F NMR. The conversion was 92.9% and the final product (I) yield was 75.6 mol %. The amounts of reagent used are summarized in Table 4. The results are summarized in Table 5.

TABLE 4

Total amounts of reagents used:

| Reagent | Mass (g) | mmol |
|---|---|---|
| CF$_3$CH$_2$OTs | 8.53 | 33.6 |
| (n-Bu)$_4$NBr | 0.97 | 3 |
| Aliquat ® 336 (Octyl)$_3$(CH$_3$)NCl | 1.19 | 2.9 |
| NaHS•H$_2$O | 7.64 | 103.2 |
| 36% HCl | 2.08 | 57.2 |

In Example 7A, the mol ratio of NaSH:CF$_3$CH$_2$OTs was 3:1 and the phase transfer catalysts were used at approximately 9 mol % each.

TABLE 5

Summary of Results from Example 7A

| Part | Cummulative Time (h) | Conversion (%) | product (I) (mol %) | (II) (mol %) | (III) (mol %) |
|---|---|---|---|---|---|
| 1 | 4 | 49.4 | 44.5 | 2.5 | 0.2 |
| 2 | 8 | 56.6 | 50.6 | 2.6 | 1.0 |
| 3 | 9 | 77.4 | 67.5 | 2.9 | 1.7 |
| 4 | 13 | 92.9 | 75.6 | 4.2 | 3.3 |

Example 7B

Reaction in a 600-cc Parr 316-SS Stirred Pressure Reactor

A 600-cc 316-SS Parr reactor was charged with CF$_3$CH$_2$OTs (40.33 g/158.6 mmol), toluene (228.56 g/2.48 mol) and Aliquat® 336 (1.33 g/3.3 mmol). Separately, NaHS.H$_2$O (35.36 g/477.5 mmol) and (n-Bu)$_4$NBr (1.01 g/3.1 mmol) were dissolved with water (40.33 g/2.2406 mol) and this aqueous mixture was subsequently added to the Parr reactor. Trifluorotoluene (2.42 g/16.6 mmol) was added to serve as an internal standard. The reactor was sealed and placed in an electrical heating mantle and the overhead stirring motor connected. Concentrated HCl (16.37 g @36%=5.89 g/161.7 mmol) was transferred to the reactor using a syringe inserted through a septum. The reaction mixture was heated to 90° C. for 4 hours and then was permitted to cool to ambient temperature overnight. Prior to sampling, the reactor was placed in dry ice and cooled to −4° C. to minimize venting during sampling. The reactor was vented to a scrubber and sampled for analysis by $^{19}$F NMR spectroscopy. The conversion was 8.4% and the product (I) yield was 8.4%. The reaction mixture was re-heated to 90° C. for an additional 16 hours and then permitted to cool overnight with stirring to ambient temperature. Prior to sampling for analysis by $^{19}$F NMR, the reactor was placed in dry ice, cooled to −20° C., and vented to a scrubber. The conversion was 32.7% and the product (I) yield was 25.6 mol %. The reactor was charged with additional nBu$_4$NBr (1.50 g/4.6 mmol) dissolved in 1.5 g water and then heated for an additional 16 hours. Following the heating time period the mixture was cooled in dry ice to −20° C., vented to scrubber, and sampled for analysis by $^{19}$F NMR spectroscopy. The conversion was 49.5% and the product (I) yield was 41.8 mol %. The reactor was subsequently charged with additional nBu$_4$NBr (5.11 g/15.8 mmol) dissolved in 5.0 g water and Aliquat® 336 (4.74 g/1.17 mmol) dissolved in 5.0 g toluene with a syringe inserted through a septum. The reaction mixture was re-heated to 90° C. for an additional 16 hours and then permitted to cool overnight with stirring to ambient temperature. Prior to sampling for analysis by $^{19}$F NMR, the reactor was placed in dry ice, cooled to −20° C., and vented to a scrubber. The conversion was 94.6% and the final product (I) yield was 71.5 mol %. The amounts of reagents used are summarized in Table 6. The results are summarized in Table 7.

TABLE 7

Experiment 7B: Total amounts of reagents used:

| Reagent | Mass (g) | mmol |
|---|---|---|
| $CF_3CH_2OTs$ | 40.33 | 158.6 |
| $(n-Bu)_4NBr$ | 7.62 | 23.5 |
| Aliquat ® 336 $(Octyl)_3(CH_3)NCl$ | 6.07 | 15.0 |
| $NaHS \cdot H_2O$ | 35.36 | 477.5 |
| 36% HCl | 5.89 | 161.7 |

In Experiment 7B, the mol ratio of $NaSH:CF_3CH_2OTs$ was 3:1 and the phase transfer catalysts; PTC $(n-Bu)_4NBr$ was used at approximately 15 mol % and Aliquat® 336 used at 9.5 mol %.

TABLE 8

Summary of Results from Example 7B

| Part | Cummulative Time (h) | Conversion (%) | product (I) (mol %) | (II) (mol %) | (III) (mol %) |
|---|---|---|---|---|---|
| 1 | 4 | 8.4 | 8.4 | — | — |
| 2 | 20 | 32.7 | 25.6 | 1.1 | 0.6 |
| 3 | 36 | 49.5 | 41.8 | 2.0 | 1.2 |
| 4 | 52 | 94.6 | 71.5 | 4.4 | 4.0 |

Example 8

The methodology (Zn/HCl) described in example 4 of U.S. Pat. No. 2,894,991 for conversion of polysulfides containing the $CF_3CH_2$ group can be used for conversion of the by-products (II) and (III) to desired product (I). That is, an aqueous combination of byproduct II and/or III and zinc could be refluxed and hydrochloric acid added while refluxing. The mixture could then be distilled to recover desired product I.

What is claimed is:

1. A method of making $CF_3CH_2SH$, comprising a step of reacting $CF_3CH_2X$, wherein X is Cl, with MSH, wherein M is an alkali metal.

2. The method of claim 1, wherein M is Na.

3. The method of claim 1, wherein the reacting is carried out in at least one organic solvent.

4. The method of claim 1, wherein the reacting is carried out in at least one polar organic solvent.

5. The method of claim 1, wherein the reacting is carried out in at least one solvent selected from the group consisting of dimethylsulfoxide, dimethylacetamide, N-methylpyrrolidone, dimethylformamide, ethylene glycol and combinations thereof.

6. The method of claim 1, wherein the reacting is carried out in the presence of a phase transfer catalyst.

7. The method of claim 6, wherein the phase transfer catalyst is a tetraalkyl ammonium salt.

8. The method of claim 7, wherein the tetraalkyl ammonium salt is selected from the group consisting of the tetra alkyl ammonium salts tetra-n-butylammonium bromide, methyltrioctylammonium chloride and mixtures thereof.

9. The method of claim 1, wherein MSH is reacted in molar excess with $CF_3CH_2X$.

10. The method of claim 1, wherein at least two moles of MSH per mole of $CF_3CH_2X$ are reacted.

11. The method of claim 1, wherein the reacting is conducted at a temperature within a range of about 70° C. to about 110° C.

12. The method of claim 1, wherein $CF_3CH_2X$ and MSH are reacted for a period of time of from about 1 hour to about 5 hours.

13. The method of claim 1, wherein the reacting is carried out at a pressure above atmospheric pressure.

14. The method of claim 1, wherein $H_2S$ is additionally present during the reacting of $CF_3CH_2X$ and MSH.

15. The method of claim 1, wherein the reacting is carried out in a sealed reactor with the $CF_3CH_2X$ and the MSH present in a liquid reaction medium and wherein sufficient $H_2S$ is present in the sealed reactor to produce a partial pressure of $H_2S$ above the liquid reaction medium greater than the saturation partial pressure.

16. The method of claim 1, wherein reacting $CF_3CH_2X$ and MSH yields a reaction product mixture comprised of $CF_3CH_2SH$ and at least one by-product selected from the group consisting of $(CF_3CH_2)_2S_2$ and $(CF_3CH_2)_2S$.

17. The method of claim 13, additionally comprising a further step of separating $CF_3CH_2X$ from the reaction product mixture.

18. The method of claim 16, additionally comprising a further step of separating the at least one by-product from the reaction product mixture.

19. The method of claim 16, additionally comprising a further step of reacting the at least one by-product separated from the reaction product mixture with a hydrogenating agent to form $CF_3CH_2SH$.

20. A method of making $CF_3CH_2SH$, comprising a step of reacting $CF_3CH_2Cl$ with a molar excess of NaSH in a reaction medium comprised of one or more polar organic solvents at a temperature of from about 70° C. to about 110° C. for a time of from about 1 to about 5 hours.

21. The method of claim 20, wherein $H_2S$ is additionally present during the reacting of $CF_3CH_2Cl$ and NaSH.

* * * * *